(12) United States Patent
Lore et al.

(10) Patent No.: US 11,237,409 B2
(45) Date of Patent: Feb. 1, 2022

(54) WEARING DETECTION MODULE FOR SPECTACLE FRAME

(71) Applicant: Essilor International, Charenton-le-Pont (FR)

(72) Inventors: Marie Lore, Charenton-le-Pont (FR); Paul Gil, Charenton-le-Pont (FR); Guillaume Broutin, Charenton-le-Pont (FR); Jean Sahler, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/711,527

(22) Filed: Sep. 21, 2017

(65) Prior Publication Data

US 2018/0081201 A1 Mar. 22, 2018

(30) Foreign Application Priority Data

Sep. 22, 2016 (EP) ..................................... 16306221

(51) Int. Cl.
*G02C 11/00* (2006.01)
*G02B 27/00* (2006.01)
(Continued)

(52) U.S. Cl.
CPC .......... *G02C 11/10* (2013.01); *A61B 5/02438* (2013.01); *A61B 5/6803* (2013.01);
(Continued)

(58) Field of Classification Search
CPC ... G02C 11/10; A61B 5/02438; A61B 5/6803; G02B 27/0093; G02B 27/017; G02B 2027/014; G02B 2027/0178
(Continued)

(56) References Cited

U.S. PATENT DOCUMENTS

2004/0104864 A1* 6/2004 Nakada ................ G02B 27/017
345/8
2011/0080289 A1* 4/2011 Minton .................. H04B 1/385
340/573.1
(Continued)

FOREIGN PATENT DOCUMENTS

WO WO 2016/142423 A1 9/2016

OTHER PUBLICATIONS

European Search Report dated May 23, 2017 in European Application 16306221.9, filed on Sep. 22, 2016 ( with Written opinion).

*Primary Examiner* — Travis S Fissel
(74) *Attorney, Agent, or Firm* — Oblon, McClelland, Maier & Neustadt, L.L.P.

(57) ABSTRACT

A wearing detection module configured to be fixed on a spectacle frame element of a smart spectacle frame, the spectacle frame element including a first surface configured to face the wearer when using the smart spectacle frame and a second surface opposed to the first surface, and the wearing detection module including a pair of sensors configured to measure one parameter indicative of the distance between the spectacle frame element and the wearer, one sensor is arranged on the first surface and the other one is arranged on the second surface, and a processing unit configured to receive data indicative of the parameter sensed (Continued)

by each sensors and to determine a wearing data indicative of the use by the wearer of the smart spectacle frame based on the received data.

14 Claims, 2 Drawing Sheets

(51) Int. Cl.
*G02B 27/01* (2006.01)
*A61B 5/024* (2006.01)
*A61B 5/00* (2006.01)
*G01B 21/16* (2006.01)
*G01J 1/42* (2006.01)
*G02C 5/14* (2006.01)
*H02S 99/00* (2014.01)
*G01B 7/14* (2006.01)
*G01B 7/32* (2006.01)
*G01S 17/08* (2006.01)

(52) U.S. Cl.
CPC ....... *G02B 27/0093* (2013.01); *G02B 27/017* (2013.01); *H02S 99/00* (2013.01); *A61B 2560/0252* (2013.01); *A61B 2562/0257* (2013.01); *G01B 7/14* (2013.01); *G01B 7/32* (2013.01); *G01B 21/16* (2013.01); *G01J 1/4204* (2013.01); *G01S 17/08* (2013.01); *G02B 2027/014* (2013.01); *G02B 2027/0178* (2013.01); *G02C 5/14* (2013.01)

(58) Field of Classification Search
USPC .................................. 359/630–634; 351/158
See application file for complete search history.

(56) References Cited

U.S. PATENT DOCUMENTS

| | | | |
|---|---|---|---|
| 2011/0249165 A1 | 10/2011 | Churei | |
| 2012/0218301 A1* | 8/2012 | Miller | G02B 27/017 345/633 |
| 2014/0145914 A1 | 5/2014 | Latta et al. | |
| 2014/0361185 A1* | 12/2014 | Howell | G02C 11/00 250/372 |
| 2015/0015847 A1* | 1/2015 | Bergman | G06F 3/013 351/209 |
| 2015/0341717 A1* | 11/2015 | Song | H04R 1/08 381/110 |
| 2016/0014129 A1* | 1/2016 | Park | A61B 5/681 726/1 |
| 2016/0041613 A1* | 2/2016 | Klanner | G06F 3/0346 345/156 |
| 2017/0032646 A1* | 2/2017 | Alameh | G01V 8/10 |
| 2017/0227779 A1* | 8/2017 | Kato | G02B 27/02 |

\* cited by examiner

WEARING DETECTION MODULE FOR SPECTACLE FRAME

FIELD OF THE INVENTION

The invention relates to a wearing detection module for spectacle frame, a spectacle frame comprising such a wearing detection module and a head mounted device comprising such a spectacle frame.

BACKGROUND OF THE INVENTION

Head mounted devices comprising electronic spectacle frames have an important and rapid growth. More and more electronic spectacle frames are being develop with a greater variety of different electronic elements.

Electronic spectacle frame may comprise many different electronic elements such as sensors, displays, active lenses, batteries, processors for local processing and communication devices, and charging devices.

With the growing interest in electronic spectacle frames, it has become important to provide a solution that allows indicating the status of the head mounted device and more particularly, if it is worn or not by the user.

It is known to embed a sensor configured to sense a parameter indicative of the distance between the spectacle frame element and the wearer.

Nevertheless, the information provided by such a sensor is not reliable enough. Indeed, many false positives can be generated, such as when the user holds the head mounted device in his hand.

Therefore, there is a need for a solution allowing to detect in a more robust manner if the head mounted device is really worn on the head of the wearer.

An aim of the present invention is to propose such solution.

SUMMARY OF THE INVENTION

To this end, the invention proposes a wearing detection module configured to be fixed on a spectacle frame element of a smart spectacle frame, the spectacle frame element comprising a first surface configured to face the wearer when using the smart spectacle frame and a second surface opposed to the first surface, and the wearing detection module comprising:
  a pair of sensors configured to measure one parameter indicative of the distance between the spectacle frame element and the wearer, one sensor is arranged on the first surface and the other one is arranged on the second surface, and
  a processing unit configured to receive data indicative of the parameter sensed by each sensors and to determine a wearing data indicative of the use by the wearer of the smart spectacle frame based on the received data.

Advantageously, the wearing detection module for spectacle frame according to the invention provides a solution for determining if a head mounted device comprising a spectacle frame is worn or not by a user.

Knowing the status of the head mounted device (worn or not) and the duration or frequencies, the wearing detection module according to the invention can advantageously help for energy consumption optimization and for the analysis of data collected in the smart spectacle frame.

This wearing detection module according to the invention eliminates all potential false positives detected by current wearing detection devices.

According to further embodiments which can be considered alone or in combination:
  at least one sensor is an infrared proximity sensor configured to emit light and to detect light reflected back;
  at least one sensor is a capacitive sensor configured to measure the contact area or the distance between the spectacle frame element and the wearer;
  at least one sensor is a temperature sensors configured to measure the temperature related to the distance between the spectacle frame element and the wearer;
  at least one sensor is a resistive sensors configured to measure biological and/or physiological parameters of the wearer;
  the spectacle frame element is a spectacle temple or a spectacle front part of a spectacle frame.

The invention also relates to a spectacle frame element for a smart spectacle frame comprising a wearing detection module according to the invention.

Another object of the invention relates to a head mounted device comprising a smart spectacle frame having a spectacle frame element according to the invention.

According to further embodiments which can be considered alone or in combination:
  the head mounted device further comprises an electronic component and a battery configured to power the electronic component and a managing unit comprising at least:
    a memory configured to store computer executable instructions; and
    a processor for executing the computer executable instructions, wherein the computer executable instructions comprise instructions for managing the power delivered by the battery to the electronic component considering the wearing data determined by the wearing detection module.
  the head mounted device further comprises a communication unit and a managing unit comprising at least:
    a memory configured to store computer executable instructions; and
    a processor for executing the computer executable instructions, wherein the computer executable instructions comprise instructions for managing the reception or emission of data by the communication unit to another communication entity considering the wearing data determined by the wearing detection module.
  the head mounted device further comprises a health monitoring device configured to be fixed on a spectacle frame, the monitoring device comprises:
    at least two light sensors configured to measure light data indicative of at least one parameter of the light received by a wearer when the head mounted device is worn by the wearer, and
    a communication unit associated with the light sensors and configured to communicate said light data to an information data generating unit,
    the information data generating unit configured to:
      receive and store said light data, and
      generate light information based on the received light data, the light information being indicative of at least the spectrum of the light received by the user, the intensity of the light received by the user, the dose of the light received by the user.
  the head mounted device further comprises an optical function controller adapted to control the optical function of the head-mounted device based on light information generated by the monitoring device.

the head mounted device further comprises an environmental light monitoring device configured to be fixed on a spectacle frame, the environmental light monitoring device comprising:
  a environmental light sensor configured to measure environmental light data indicative of at least one parameter of the light in the environment of the head mounted device, and
  a communication unit associated with the environmental light sensor and configured to communicate said environmental light data to an environmental information data generating unit,
  the information data generating unit configured to:
    receive and store said environmental light data, and
    generate environmental light information based on the received environmental light data, the environmental light information being indicative of at least the spectrum, the intensity, the dose of the light in the environment of the head mounted device,
wherein the environmental light monitoring device further comprises a solar cell arranged for receiving light and for converting the energy of received light into electricity capable to power at least the environmental light sensor, the communication unit and the information data generating unit.

BRIEF DESCRIPTION OF THE DRAWINGS

Embodiments of the invention will now be described, by way of examples only, and with reference to the following drawings in which.

Elements in the figures are illustrated for simplicity and clarity and have not necessarily been drawn to scale. For example, the dimensions of some of the elements in the figure may be exaggerated relative to other elements to help improve the understanding of the embodiments of the present invention.

DETAILED DESCRIPTION OF PREFERRED EMBODIMENTS

Figure 1:
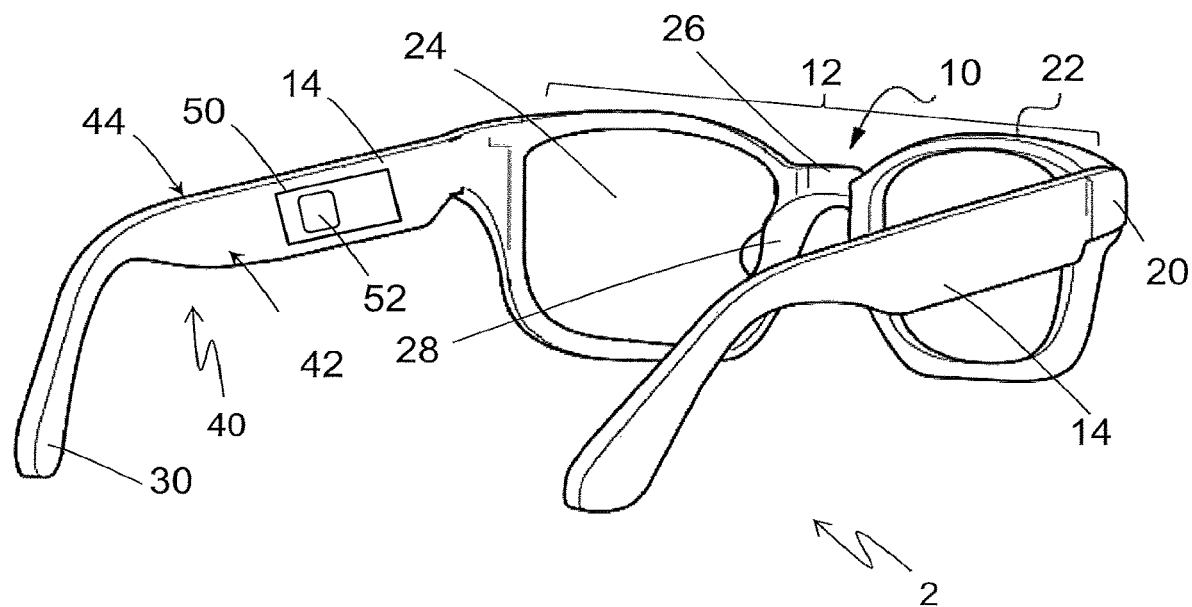
FIG. 1 is a schematic representation of an embodiment of a head mounted device according to the invention.

FIG. 1 represents an example of a head mounted device 2 according to the invention, the head mounted device 2 comprising a spectacle frame 10.

The spectacle frame 10 comprises a front part 12, a first and second temples 14.

The first and second temples 14 are configured to be attached to the front part 12 using hinges 20 and screws.

As represented on FIG. 1, the front part 12 may comprise frame rims 22 arranged to receive optical lenses 24, for example ophthalmic lenses. The frame rims are linked by a bridge 26 and may comprise nose pad 28 arranged to rest on the nose of the user when the frame in worn.

In the sense of the invention, the term "optical lens" is to be understood to mean any type of known lens intended to be supported by a wearer's face. The term can refer to ophthalmic lenses such as corrective lenses, non-corrective lenses, semi-finished lenses, such as progressive addition lenses, unifocal or multifocal lenses. The term can also refer to said ophthalmic lenses which could present at least one added value such as, for example, tint, photochromism, polarization filtering, electrochromism, antireflective properties, antiscratch properties . . . .

The head mounted device may comprise a single optical lens covering either both eyes of the wearer, for example goggles or masks, or only one eye, for example a head mounted display. The optical equipment may comprise two optical lenses each covering an eye of the wearer. The term can refer to ophthalmic optical equipment, non-ophthalmic optical equipment, sunglasses, glasses for sporting applications such as goggles, reading glasses, protective glasses, driving glasses.

The first and second temples may comprise tips 30 arranged to fit around the ears of a user when the frame is being worn by said user.

The spectacle frame 10 is a smart spectacle frame, i.e. comprising at least an electronic component embodied in at least one spectacle frame element 40. For example, the spectacle frame element is one of the spectacle temples, one of the spectacle tips, one of the hinges or the spectacle front part of a spectacle frame.

The head mounted device 2 according to the invention comprises a wearing detection module 50 of the invention fixed to a spectacle frame element 40.

Such wearing detection module 50 according to the invention will be detailed hereinafter.

Figure 2:
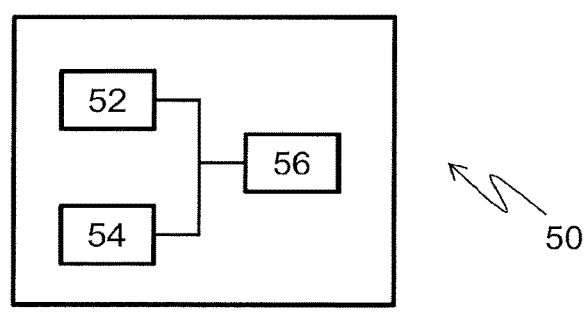
FIG. 2 is a schematic representation of a wearing detection module according to the invention.
Figure 3:
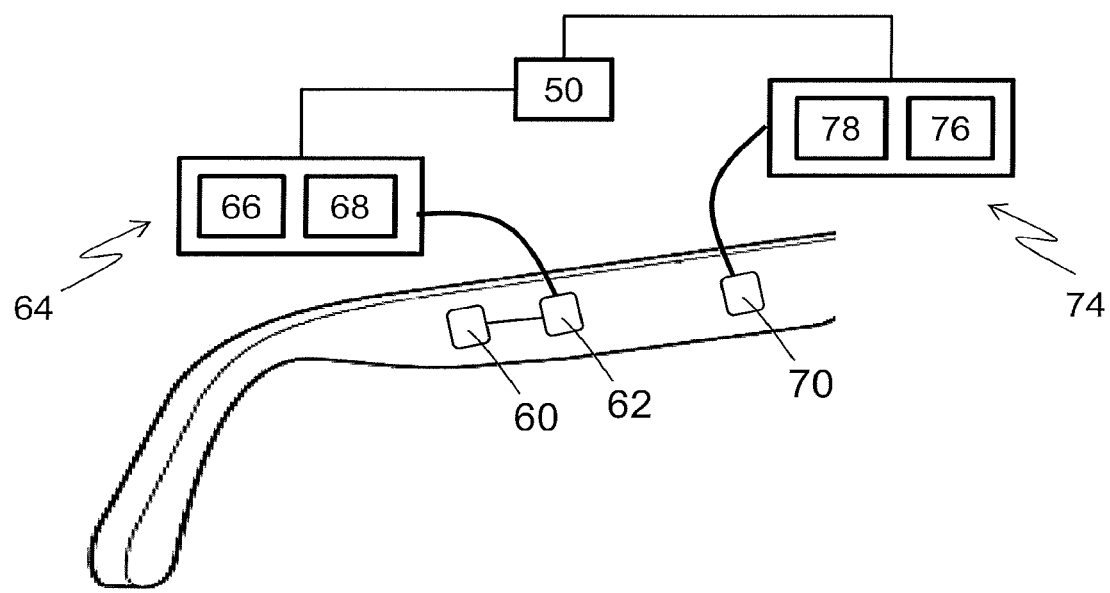
FIG. 3 illustrates another embodiment of a head mounted device according to the invention.
Figure 4:
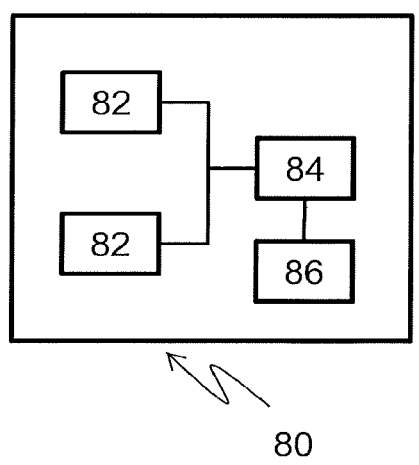
FIG. 4 is a schematic representation of a health monitoring device according to the invention.
Figure 5:
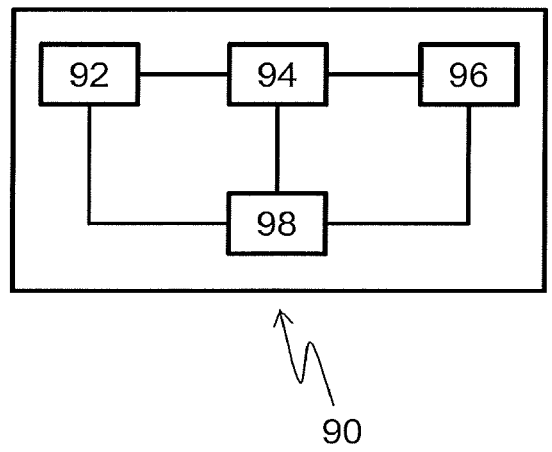
FIG. 5 is a schematic representation of an environmental light monitoring device according to the invention.

FIG. 2 illustrates an example of a wearing detection module 50 according to the invention. The wearing detection module 50 is configured to be fixed on a spectacle frame element 40 of a smart spectacle frame 10. In the example illustrated on FIG. 2, the spectacle frame element is a spectacle temple 14.

The spectacle frame element 40 comprises a first surface 42 configured to face the wearer when using the smart spectacle frame and a second surface 44 opposed to the first surface 42.

The wearing detection module 50 comprises a pair of sensors 52, 54 configured to measure one parameter indicative of the distance between the spectacle frame element 40 and the wearer. One sensor 52 is arranged on the first surface 42 and the other one 54 is arranged on the second surface 44.

The wearing detection module 50 further comprises a processing unit 56 configured to receive data indicative of the parameter sensed by each sensor 52, 54.

Furthermore, the processing unit 56 is further configured to determine a wearing data indicative of the use by the wearer of the smart spectacle frame based on the received data.

In the sense of the invention, the term "use by the wearer of the smart spectacle frame" means that the smart spectacle frame is effectively worn by the wearer and in use by the wearer. Thus, the smart spectacle frame is on the head of the wearer such that the optical lens is placed in front of at least one eye of the wearer. Specifically, the smart spectacle frame is not in a hand of the user or another person, nor placed next to an electronic device.

According to a first embodiment, at least one sensor 52, 54 is an infrared proximity sensor configured to emit light and to detect light reflected back. An infrared proximity sensor placed on the temple of the spectacle frame can indicate if the head mounted device is worn or not. If the head mounted device is not worn, no light is reflected. Such sensors may be easily embedded in the spectacle frame element.

According to a second embodiment, at least one sensor 52, 54 is a capacitive sensor configured to measure the contact area or the distance between the spectacle frame element and the wearer. Such a capacitive sensor has the advantage of being sensitive.

According to a third embodiment, at least one sensor 52, 54 is a temperature sensors configured to measure the temperature related to the distance between the spectacle frame element and the wearer. Such temperature sensors are very sensitive.

For example, if both sensors of the pair are temperature sensors, the processing of the data sensed by each temperature sensor is simply. Indeed, the detection of a difference of temperature between the two sensors is a signature of the fact that the head mounted device is worn.

According to a fourth embodiment, at least one sensor 52, 54 is a resistive sensor configured to measure biological and/or physiological parameters of the wearer.

For example, the resistive sensor may be a heart rate sensor capable of detecting heart beats in a part of a spectacle frame element close to the skin of the wearer. Such a resistive sensor has the advantage to be specific by discriminating living things and objects.

The heart rate sensor is preferably arranged on the temple 14, at the extremity of the tip 30 of the temple facing a temporal bone of the wearer or on the bridge 26

According to an embodiment of the head mounted device of the invention, the head mounted device 2 further comprises an electronic component 60 and a battery 62. The battery 62 is configured to power the electronic component 60. For example, the electronic component 60 is a sensor, an eye tracking device, a communication unit.

The electronic component 60 and the battery 62 are preferably embedded in the smart spectacle frame.

The head mounted device 2 further comprises a managing unit 64 comprising at least a memory 66 and a processor 68. The managing unit 64 is configured and arranged to manage the power delivered by the battery 62 to the electronic component 60.

The managing unit 64 is preferably also embodied in the smart spectacle frame 10 of the head mounted device 2.

The memory 66 is configured to store computer executable instructions executable by the processor 68.

The computer executable instructions comprise instructions for managing the power delivered by the battery 62 to the electronic component 60 considering the wearing data determined by the wearing detection module 50.

Thus, when the wearing detection module 50 detects that the head mounted device 2 is not worn on the head of the user, the managing unit manage the battery 62 such that the battery 62 delivers a minimum power or a null power to the electrical component 60.

According to another embodiment compatible with the previous one, the head mounted device 2 further comprises a communication unit 70.

The head mounted device 2 further comprises a managing unit 74 comprising at least a memory 76 and a processor 78. The managing unit 74 is configured and arranged to manage the communication unit 70, and more particularly data emission to and reception from a communication entity. For example, the communication entity can be a sensor, another communication unit, a data processing unit. The communication entity may be distant from the head mounted device or embedded in the head mounted device.

The communication unit 70 and/or the managing unit 74 are preferably also embodied in the head mounted device.

The memory 76 is configured to store computer executable instructions executable by the processor 78.

The computer executable instructions comprise instructions for managing the reception or emission of data by the communication unit 70 to another communication entity considering the wearing data determined by the wearing detection module.

For example, the managing unit 74 can be configured to allow the transfer of data between the communication unit 70 and the communication entity only when the wearing detection module 50 detects that the head mounted device 2 is not worn on the head of the user.

According to another embodiment compatible with the previous ones, the head mounted device 2 further comprises a health monitoring device 80 configured to be fixed on the spectacle frame of the head mounted device 2.

The monitoring device 80 comprises at least two light sensors 82 configured to measure light data indicative of at least one parameter of the light received by the wearer when the head mounted device is worn by the wearer.

Furthermore, the monitoring device 80 comprises a communication unit 84 associated with the light sensors 82 and configured to communicate said light data to an information data generating unit 86 of the monitoring device 80.

The information data generating unit 86 is configured to receive and store said light data, and to generate light information based on the received light data. The light information is indicative of at least:

the spectrum of the light received by the user,
the intensity of the light received by the user,
the dose of the light received by the user.

Preferably, the head mounted device 2 further comprises an optical function controller 88 adapted to control the optical function of the head-mounted device based on light information generated by the monitoring device.

In the sense of the invention, the optical function corresponds to a function providing for each gaze direction the effect of the optical lens on the light ray passing through the optical lens. The optical function may comprise as dioptric function, light absorption, polarizing capability, reinforcement of contrast capacity, etc . . . . The dioptric function corresponds to the optical lens power (mean power, astigmatism etc . . . ) as a function of the gaze direction.

Preferably, the light sensors 82 are configured to measure blue light data indicative of at least one parameter of the light having a wavelength comprised in a range specifically around the chronobiological blue-violet light and toxic blue-violet light.

Indeed, screens, LED and cold lamps emit a blue-violet light which can cause in the long run vision problems that are difficult to remedy. Monitoring exposure on a regular basis would help manage doses and exposure.

For example, for chronobiological turquoise light, it is a question of timing. It is beneficial in the morning because it contributes to boost alertness and energy. On the contrary, being exposed in the evening could be damageable for the quality of your sleep and disturb your sleep/wake cycles.

Thus, measuring exposure to UV radiations is also very important to monitor on a daily basis. Sunlight provides the heat and light that enhance the overall feeling of well-being and stimulate blood flow. Some UV radiations are essential to the body because it stimulates the production of vitamin D. It has an important role since it increases the absorption of calcium and phosphorus in food and plays a decisive role in skeletal development, immune function and the formation of blood elements. There is no doubt that a little sunlight is good for health. Five to fifteen minutes of casual sun exposure of hands, face and arms two or three times a week are enough to keep high concentrations of vitamin D. Near the equator, where UV intensity is higher, even shorter exposure periods are sufficient.

Toxic blue light has a central wavelength equal to 425-440 nm and the bandwidth extends on 50 nm.

Chronobiological blue light has a central wavelength equal to 490 nm and the bandwidth extends on 40 nm.

UVA and UVB radiations have respectively a central wavelength equal to 360 nm and 300 nm and both have a bandwidth extending on 60 nm.

Advantageously, the health monitoring device 80 according to the invention allows to monitor the health of the wearer regarding retinal toxicity and circadian cycle and/or exposure to UV, and to prevent effects of blue light by controlling their behavior.

Then, the light information generated can alert the consumer and a solution can be proposed to reduce this risk, for example recommending the wearer and/or the practitioner to perform action, for example reducing exposure, performing an additional treatment, such as filtering, light therapy or medication route.

According to an embodiment, the health monitoring device 80 can further comprise at least another sensor, for example:
- an actimeter configured to monitor the wearer's physiological sleep cycle and evaluate "continuously" (item every minute) its vigilance and sleep quality,
- a location-based and/or timing schedule,
- a blink detection sensor to monitor alertness, focus and fatigue level.

Preferably, the light information generated by the information data generating unit 86 is further based on wearer data relating to the age of the wearer and/or the biological clock of the wearer and/or the activity of the wearer and/or ocular disease of the wearer and/or the type of physiological disorder of the wearer.

According to another embodiment compatible with the previous ones, the head mounted device 2 further comprises an environmental light monitoring device 90 configured to be fixed on a spectacle frame of the head mounted device 2.

The environmental light monitoring device 90 comprises an environmental light sensor 92 configured to measure environmental light data indicative of at least one parameter of the light in the environment of the head mounted device.

Furthermore, the environmental light monitoring device 90 comprises a communication unit 94 associated with the environmental light sensor 92 and configured to communicate said environmental light data to an environmental information data generating unit 96 of the environmental light monitoring device 90.

The information data generating unit 96 is configured to receive and store said environmental light data, and to generate environmental light information based on the received environmental light data.

The environmental light information is indicative of at least the spectrum, the intensity, the dose of the light in the environment of the head mounted device 2.

The environmental light monitoring device 90 further comprises a solar cell 98 arranged for receiving light and for converting the energy of received light into electricity capable to power at least the environmental light sensor 92, the communication unit 94 and the information data generating unit 96.

Indeed, when there is enough electricity, the processor "wakes up", makes the light measurements and sends the data for example with bluetooth low energy, then sleeps until there is enough electricity to start again.

Thanks to the solar cell 98, such an environmental light monitoring device 90 can be used independently, without a head mounted device. Indeed, the environmental light monitoring device 90 could be embeddable in wearables such as wristbands, headbands or in a sticker.

Such an environmental light monitoring device allows measuring environmental light parameters (UV level, XYZ colors, bad blue light or good blue light, specific spectral range, infrared . . . ) with a tiny and autonomous system, i.e. without using a battery and a battery charger.

In a distant receiver device, all the measurements can be stored. For example, if the receiver device has no data that means there is not enough light or UV. Furthermore, if the environmental light monitoring device further comprises a location mean such as a GPS system, all the measurements made by a plurality of environmental light monitoring device can be localized and a real time light map over the world may be created.

Preferably, the environmental light monitoring device 90 further comprises a supercapacitor to accumulate the energy before using it or a little battery between the solar cell 98 and a processor of the information data generating unit 96.

For example, the environmental light monitoring device according to the invention could ideally be integrated in sunglasses to get measurement of specific wavelengths of light, along with a mobile application that can get the light data and display it on the smartphone.

For another example, a mobile application embedded in a smartphone can scan all environmental light monitoring devices embedded in stickers placed around the user of the smartphone and give the UV index or any other light measurements, even if you don't have a sticker on the user.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A wearing detection module configured to be fixed on a spectacle frame element positioned on one side of a smart spectacle frame, the spectacle frame element comprising a first surface that faces a wearer when using the smart spectacle frame and a second surface opposed to the first surface that does not face the wearer when using the smart spectacle frame, the wearing detection module comprising:
   a pair of sensors arranged on opposite surfaces of the spectacle frame element and each configured to measure a distance between the spectacle frame element and the wearer, one sensor is arranged on the first surface of the spectacle frame element that faces the wearer when using the smart spectacle frame and the other sensor is arranged on the second surface of the spectacle frame element that does not face the wearer when using the smart spectacle frame, both sensors positioned on a same side of the wearer's head; and processing circuitry configured to receive data of the distance sensed by each of the sensors and to determine wearing data indicative of use by the wearer of the smart spectacle frame based on the received data.

2. The wearing detection module according to claim 1, wherein at least one sensor of the pair of sensors is an infrared proximity sensor configured to emit light and to detect light reflected back.

3. The wearing detection module according to claim 1, wherein at least one sensor of the pair of sensors is a capacitive sensor configured to measure a contact area or the distance between the spectacle frame element and the wearer.

4. The wearing detection module according to claim 1, wherein at least one sensor of the pair of sensors is a temperature sensor configured to measure a temperature related to the distance between the spectacle frame element and the wearer.

5. The wearing detection module according to claim 1, wherein at least one sensor of the pair of sensors is a resistive sensor configured to measure biological and/or physiological parameters of the wearer.

6. The wearing detection module according to claim 1, wherein the spectacle frame element is a spectacle temple or a spectacle front part of the smart spectacle frame.

7. A spectacle frame element for a smart spectacle frame comprising the wearing detection module according to claim 1.

8. A head mounted device comprising:
a smart spectacle frame having a spectacle frame element positioned on one side of the smart spectacle frame that includes a first surface that faces a wearer when using the smart spectacle frame and a second surface opposed to the first surface that does not face the wearer when using the smart spectacle frame, the spectacle frame element including a wearing detection module configured to be fixed on the spectacle frame element, the wearing detection module including
a pair of sensors arranged on opposite surfaces of the spectacle frame element and each configured to measure a distance between the spectacle frame element and the wearer, one sensor is arranged on the first surface of the spectacle frame element that faces the wearer when using the smart spectacle frame and the other sensor is arranged on the second surface of the spectacle frame element that does not face the wearer when using the smart spectacle frame, both sensors positioned on a same side of the wearer's head, and
processing circuitry configured to receive data of the distance sensed by each of the sensors and to determine wearing data indicative of use by the wearer of the smart spectacle frame based on the received data.

9. The head mounted device according to claim 8, further comprising an electronic component and a battery configured to power the electronic component and a managing unit comprising at least:
a non-transitory memory configured to store computer executable instructions, and
a processor for executing the computer executable instructions, wherein the computer executable instructions comprise instructions for managing the power delivered by the battery to the electronic component considering the wearing data determined by the wearing detection module.

10. The head mounted device according to claim 8, further comprising a communication device and a managing unit comprising at least:
a non-transitory memory configured to store computer executable instructions, and
a processor for executing the computer executable instructions, wherein the computer executable instructions comprise instructions for managing the reception or emission of data by the communication device to another communication entity considering the wearing data determined by the wearing detection module.

11. The head mounted device according to claim 8, further comprising a health monitoring device configured to be fixed on the spectacle frame, wherein the monitoring device comprises:
at least two light sensors configured to measure light data indicative of at least one parameter of light received by the wearer when the head mounted device is worn by the wearer, and
a communication device associated with the light sensors and configured to communicate said light data to an information data generator,
the information data generator configured to:
receive and store said light data, and
generate light information based on the received light data, the light information being indicative of at least spectrum of the light received by the wearer, intensity of the light received by the wearer, dose of the light received by the wearer.

12. The head mounted device according to claim 11, wherein the head mounted device further comprises an optical function controller configured to control an optical function of the head-mounted device based on light information generated by the monitoring device.

13. The head mounted device according to claim 8, further comprising an environmental light monitoring device configured to be fixed on the spectacle frame, wherein the environmental light monitoring device comprises:
a environmental light sensor configured to measure environmental light data indicative of at least one parameter of light in an environment of the head mounted device, and
a communication device associated with the environmental light sensor and configured to communicate said environmental light data to an environmental information data generator,
the information data generator configured to:
receive and store said environmental light data, and
generate environmental light information based on the received environmental light data, the environmental light information being indicative of at least spectrum, intensity, dose of the light in the environment of the head mounted device,
wherein the environmental light monitoring device further comprises a solar cell arranged to receive light and to convert energy of received light into electricity capable to power at least the environmental light sensor, the communication device and the information data generator.

14. The wearing detection module according to claim 1, wherein the spectacle frame element is a spectacle temple of the smart spectacle frame such that the one sensor is arranged on the first surface of the spectacle temple that faces the wearer when using the smart spectacle frame and the other sensor is arranged on the second surface of the spectacle temple that does not face the wearer when using the smart spectacle frame.

* * * * *